(12) United States Patent
Morello et al.

(10) Patent No.: US 9,861,729 B2
(45) Date of Patent: Jan. 9, 2018

(54) ARTIFICIAL HEART SYSTEM

(75) Inventors: Gino Morello, Houston, TX (US); Robert Benkowski, Houston, TX (US)

(73) Assignee: Reliant Heart Inc., Houston, TX (US)

( * ) Notice: Subject to any disclaimer, the term of this patent is extended or adjusted under 35 U.S.C. 154(b) by 1243 days.

(21) Appl. No.: 11/916,958

(22) PCT Filed: Jun. 8, 2006

(86) PCT No.: PCT/US2006/022475
§ 371 (c)(1),
(2), (4) Date: Sep. 10, 2008

(87) PCT Pub. No.: WO2006/133409
PCT Pub. Date: Dec. 14, 2006

(65) Prior Publication Data
US 2009/0156885 A1 Jun. 18, 2009

Related U.S. Application Data

(60) Provisional application No. 60/595,131, filed on Jun. 8, 2005.

(51) Int. Cl.
*A61M 1/10* (2006.01)
*A61M 1/12* (2006.01)
(52) U.S. Cl.
CPC .......... *A61M 1/1086* (2013.01); *A61M 1/101* (2013.01); *A61M 1/1031* (2014.02); *A61M 1/122* (2014.02)

(58) Field of Classification Search
CPC .... A61M 1/10; A61M 1/1037; A61M 1/1086; A61M 1/12; A61M 1/106; A61M 1/127; A61M 2205/3334; A61M 1/1087; A61M 1/1096; A61M 2205/8243; A61M 1/122; A61M 1/1044
USPC ..................... 600/16, 17; 623/3.28
See application file for complete search history.

(56) References Cited

U.S. PATENT DOCUMENTS

| | | | | |
|---|---|---|---|---|
| 4,662,358 A * | 5/1987 | Farrar et al. | | 600/16 |
| 5,964,694 A * | 10/1999 | Siess et al. | | 600/17 |
| 6,139,487 A * | 10/2000 | Siess | | 600/16 |
| 2001/0037093 A1* | 11/2001 | Benkowski et al. | | 604/288.01 |
| 2003/0069465 A1* | 4/2003 | Benkowski et al. | | 600/16 |

OTHER PUBLICATIONS

International Search Report for corresponding International Patent Application No. PCT/US06/22475.
Written Opinion for corresponding International Patent Application No. PCT/US06/22475.

* cited by examiner

*Primary Examiner* — Carl H Layno
*Assistant Examiner* — Jon Eric C Morales
(74) *Attorney, Agent, or Firm* — Sutton McAughan Deaver PLLC

(57) ABSTRACT

A blood pump system includes two blood pumps, which may be implanted into a patient. The blood pumps may comprise VAD pumps. Control devices and methods operate the pumps such that they can function as a total artificial heart.

21 Claims, 7 Drawing Sheets

ARTIFICIAL HEART SYSTEM

CROSS-REFERENCE TO RELATED APPLICATION

This application claims the benefit of and priority to PCT Application No. PCT/US2006/022475, filed on Jun. 8, 2006, and U.S. Provisional Patent Application No. 60/595,131, filed on Jun. 8, 2005, the entire disclosure of each of which is incorporated by reference.

BACKGROUND

The invention relates generally to artificial heart systems.

Artificial heart system and other implantable blood pump systems are generally employed either to completely replace a human heart that is not functioning properly, or to boost blood circulation in patients whose heart still functions but is not pumping blood at an adequate rate. Known implantable blood pump systems are primarily used as a "bridge to transplant." In other words, existing blood pump system applications are mainly temporary fixes, intended to keep a patient alive until a donor is available. However, the shortage of human organ donors, coupled with improvements in blood pump reliability make long-term, or even permanent blood pump implementations a reality.

The present disclosure addresses shortcomings associated with the prior art.

SUMMARY

A heart pump system induces first and second blood pumps with a controller operably connected to the first and second pumps, such that the pumps are operable as a total artificial heart. The controller may first and second controllers operably connected to the first and second pumps, respectively. In certain exemplary embodiments, the pumps are ventricle assist devices, wherein the first pump is inserted between a patient's left atrium and ascending aorta and the second pump is inserted between the patient's right atrium and pulmonary artery. The pumps can be operated, for example, in a master/slave configuration.

BRIEF DESCRIPTION OF THE DRAWINGS

Other objects and advantages of the invention will become apparent upon reading the following detailed description and upon reference to the drawings in which.

Figure 1:
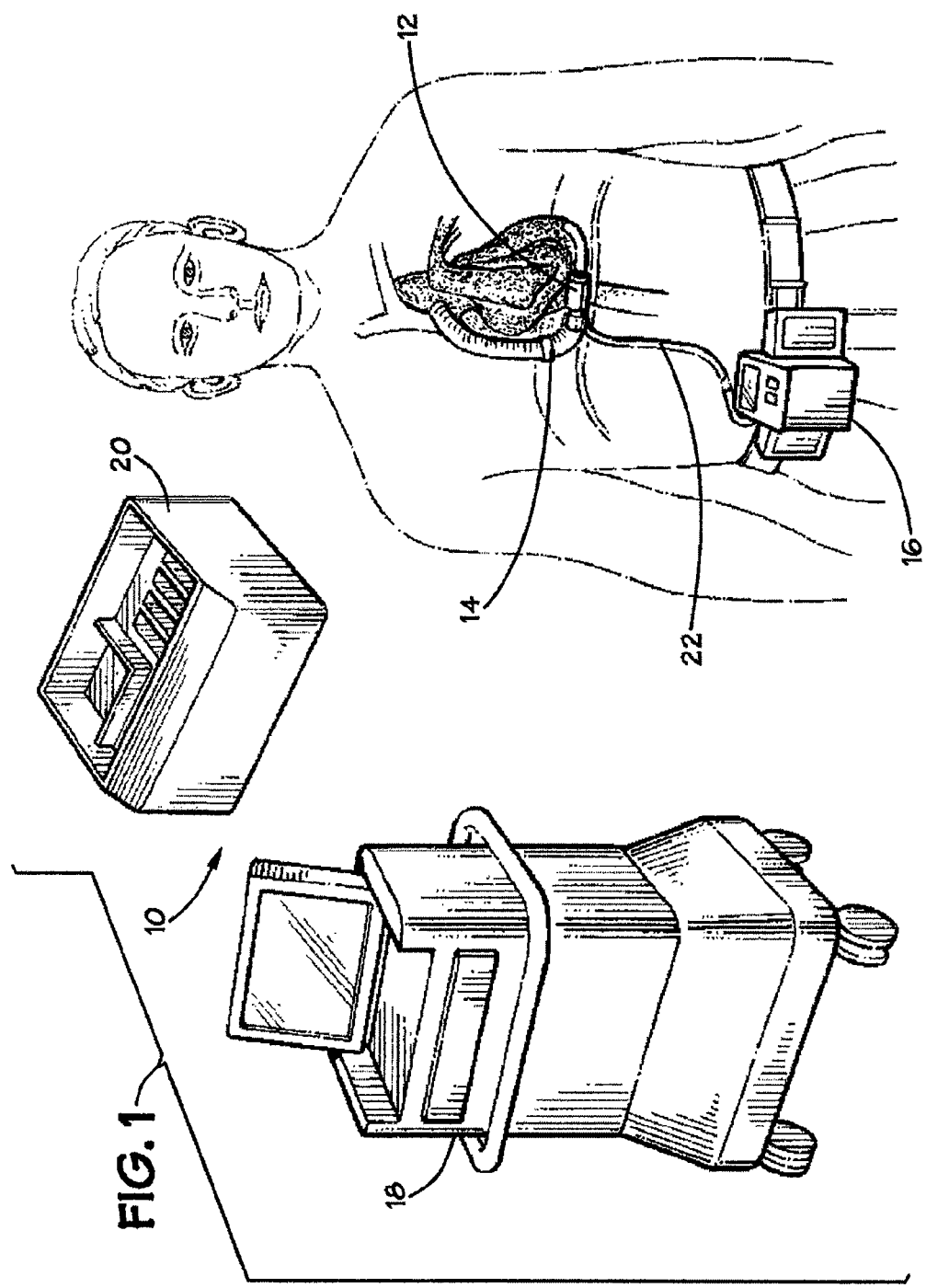
FIG. 1 is a block diagram of a heart pump system in accordance with certain teachings of the present disclosure.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

FIG. 1 shows an exemplary heart pump system 10, which as shown, functions as a left ventricle assist device (LVAD). The system 10 includes components designed to be implanted within a human body and components external to the body. The components of the system 10 that are implantable include a rotary pump 12 (or "VAD pump") and a flow sensor 14. The external components include a portable controller module 16, a clinical data acquisition system (CDAS) 18, and a patient home support system (PHSS) 20. The implanted components are connected to the controller module 16 via a percutaneous cable 22. The controller module 16 may be mounted to a support device, such as a user's belt 23 or to a vest worn by the user. Alternatively, the controller module 16 may be placed on the CDAS 18 or placed on a nightstand when the user is in bed. A spare controller module 16 may be stored in the PHSS 20. The controller module 16 includes two connectors 24 and 26 for coupling to one or more batteries 28, which provide power for the controller module 16 when in a stand-alone mode. The system 10 may further include a battery charger (not shown in FIG. 1). The same connectors 24, 26 also may couple the controller module to either the CDAS 18 or PHSS 20.

In accordance with certain teachings of the present disclosure, two of the pumps 12 are implanted to form a total artificial heart (TAH) system. Suitable pumps include various embodiments of pumps disclosed in U.S. Pat. No. 5,527,159; 5,947,892 or 5,692,882; all of which are incorporated by reference. Exemplary implantable pump systems and control methods are disclosed in U.S. Pat. Nos. 6,652,447; 6,605,032 and 6,183,412; also incorporated by reference. Other versions employ an implantable centrifugal pump or a pulsatile pump.

In the TAH system, two of the pumps 12 are implanted to function as an artificial heart, providing mechanical assistance in patients who suffer both right side and left side heart failure. The pumps 12 can provide biventricular support with one attached to the right ventricle and one attached to the left ventricle. The native ventricles are surgically dissected and the remaining atria utilized as blood filled reservoirs and as points of attachment for the inlets of the pumps.

Figure 2:
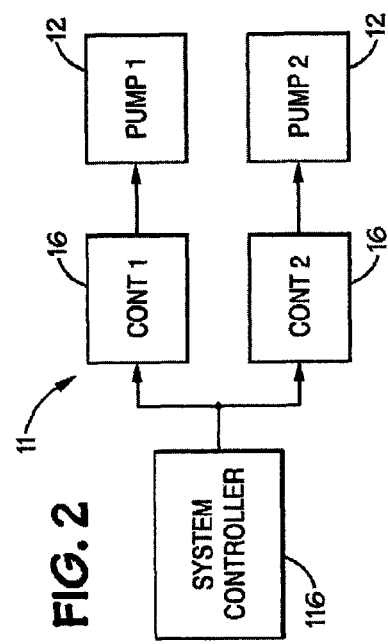
FIG. 2 is a block diagram conceptually illustrating portions of an artificial heart system in accordance with the teachings of the present disclosure.

FIG. 2 conceptually illustrates portions of a TAH system 11, which includes two pumps 12 connected to respective controllers 16 with a system controller 116 connected to the pump controllers 16. The system controller 116 and pump controllers 16 may be implemented by a single device, or the functions of the pump controllers 16 could be combined into a single device connected to the system controller 116.

Figure 3:
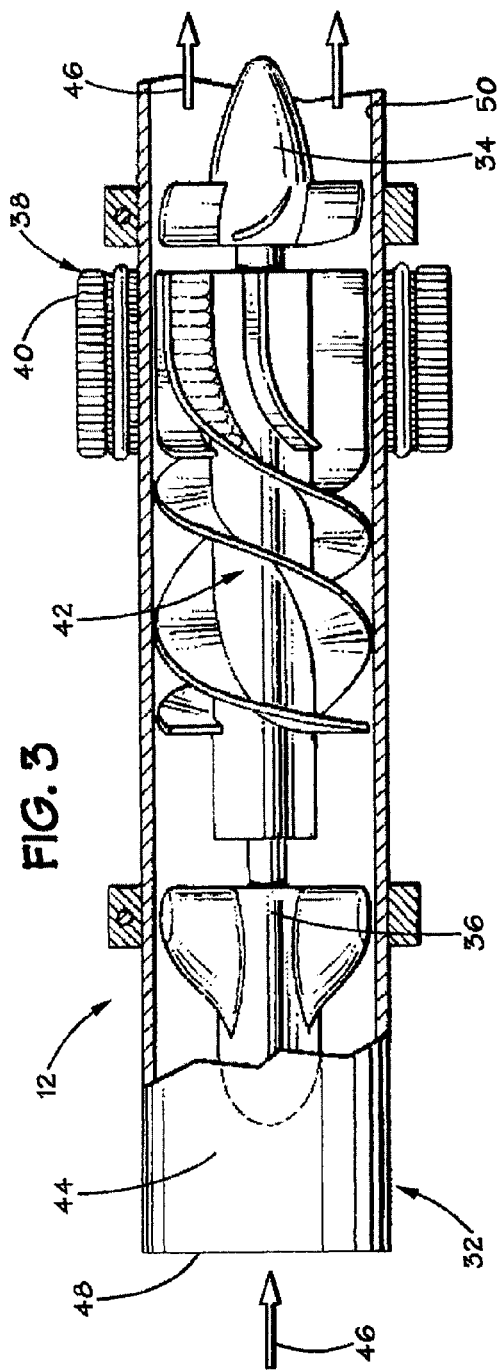
FIG. 3 illustrates an exemplary heart pump suitable for use in accordance with the teachings herein.

An example of a blood pump 12 suitable for use as part of a TAH system is illustrated in FIG. 3. The exemplary pump includes a pump housing 32, a diffuser 34, a flow straightener 36, and a brushless DC motor 38, which includes a stator 40 and a rotor 42. The housing 32 includes a flow tube 44 having a blood flow path 46 therethrough, a blood inlet 48, and a blood outlet 50.

The stator 40 is attached to the pump housing 32, is preferably located outside the flow tube 44, and has a stator field winding 52 for producing a stator magnetic field. In one embodiment, the stator 40 includes three stator windings and may be three phase "Y" or "Delta" wound. The flow straightener 36 is located within the flow tube 44, and includes a flow straightener hub 54 and at least one flow straightener blade 56 attached to the flow straightener hub 54. The rotor 42 is located within the flow tube 44 for rotation in response to the stator magnetic field, and includes an inducer 58 and an impeller 60. Excitation current is applied to the stator windings 52 to generate a rotating magnetic field. A plurality of magnets 62 are coupled to the rotor 42. The magnets 62, and thus the rotor 42, follow the rotary field to produce rotary motion.

The inducer 58 is located downstream of the flow straightener 36, and includes an inducer hub 64 and at least one inducer blade 66 attached to the inducer hub 64. The impeller 60 is located downstream of the inducer 58, and includes an impeller hub 68 and at least one impeller blade 70 attached to the impeller hub 68. The diffuser 34 is located within the flow tube 44 downstream of the impeller 60, and includes a diffuser hub 72 and at least one diffuser blade 74 attached to the diffuser hub 72. The exemplary pump further includes a front bearing assembly 76 attached to the flow straightener hub 36.

In the TAH system 11, left side support is provided by a single pump 12 inserted between the left atrium and ascending aorta while right side support is provided by another pump 12 inserted between the right atrium and pulmonary artery. The patient's native ventricles are removed prior to implantation of the devices. A biventricular assist device may be realized by leaving the ventricles intact and modifying the control algorithms accordingly.

Figure 4:
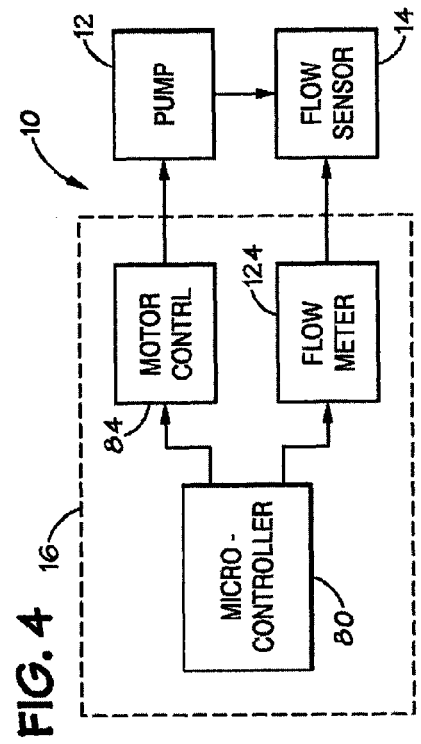
FIG. 4 illustrates portions of a pump and pump controller in accordance with the teachings of the present disclosure.
Figure 5:
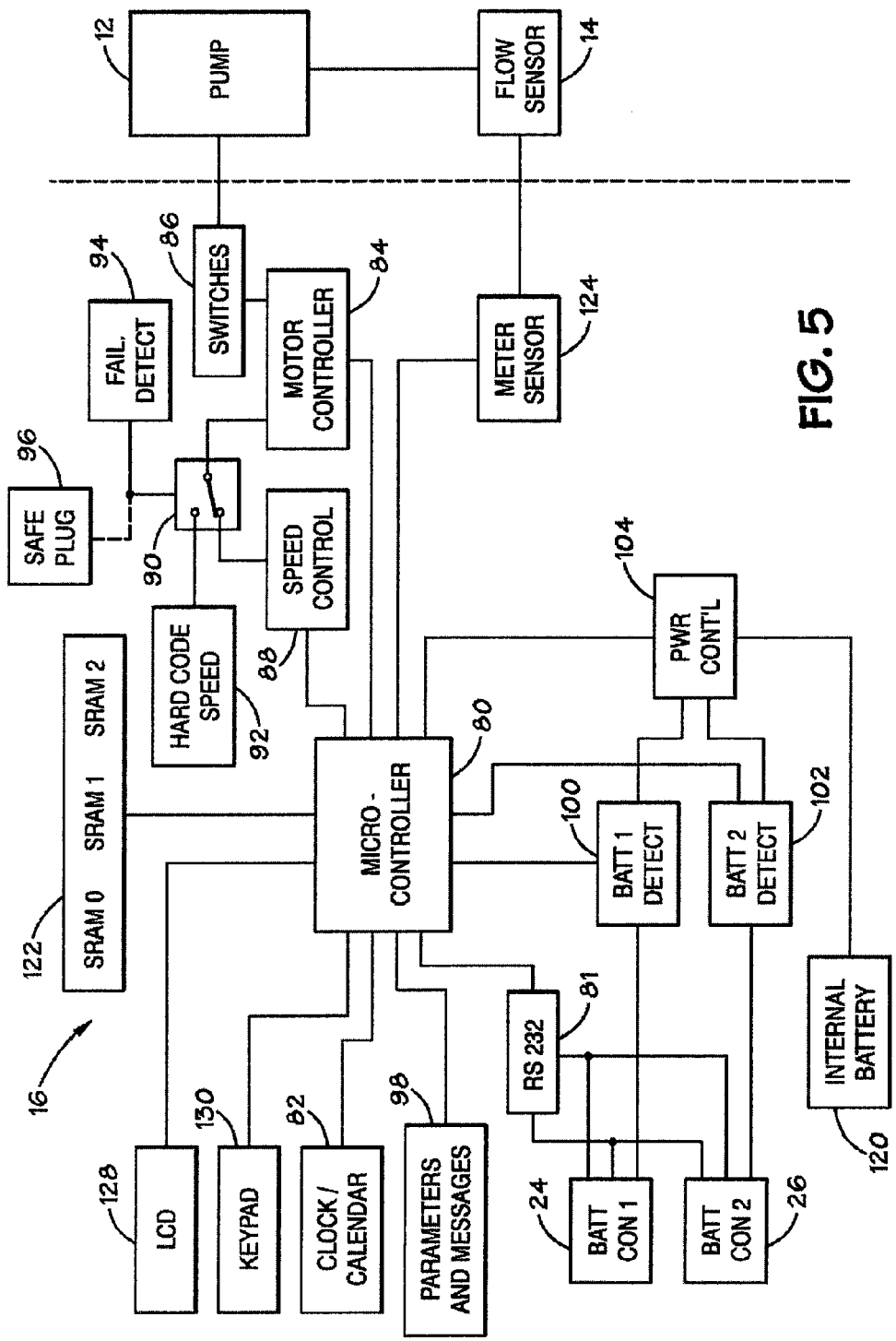
FIG. 5 illustrates additional details of the exemplary pump controller shown in FIG. 4.

The pump controller 16 of an embodiment of the present system is illustrated in greater detail in FIGS. 4 and 5 in block diagram form. As noted above, a single pump controller 16 may be configured to control both pumps 12, or two pump controllers 16 may be used. The pump controller 16 includes a processor, such as a microcontroller 80, which is coupled to a communications device 81 such as an RS-232 driver/receiver as is known in the art, and a hardware clock and calendar device 82, which contains clock and date information, allowing the controller module 16 to provide real-time clock and calendar information. The microcontroller 80 communicates with the hardware clock 82 via the I²C protocol. The microcontroller 80 also is programmed with a selftest routine, which is executed upon application of power to check components of the controller module 16.

The controller module 16 includes first and second connectors 24, 26 for coupling the controller module 16 to a power source, such as a battery 28, or the CDAS 18 or PHSS 20. In an embodiment of the invention, the connectors 24, 26 include a break-away feature, such that the connectors 24, 26 disengage themselves if a given force is applied. For example, if a battery pack connected to the controller module 16 falls on the floor, the connector will disengage rather than pull the controller module and in turn, tug on the percutaneous cable.

A motor controller 84 is coupled to the microcontroller 80, and the motor controller 84 is coupled to the pump 12. The operation of the brushless DC motor 38 used in certain embodiments requires that current be applied in a proper sequence to the stator windings 52. Two stator windings 52 have current applied to them at any one time, and by sequencing the current on and off to the respective stator windings 52, a rotating magnetic field is produced. In an embodiment of the invention, the motor controller 84 senses back electro motive force (EMF) voltage from the motor windings 52 to determine the proper commutation phase sequence using phase lock loop (PLL) techniques. Whenever a conductor, such as a stator winding 52, is "cut" by moving magnetic lines of force, such as are generated by the magnets 62 of the brushless DC motor 38, a voltage is induced. The voltage will increase with rotor speed 42. It is possible to sense this voltage in one of the three stator windings 52 because only two of the motor's windings 52 are activated at any one time, to determine the rotor 42 position.

An alternative method of detecting the rotor 42 position relative to the stator 40 for providing the proper stator winding 52 excitation current sequence is to use a position sensor, such as a Hall effect sensor (not shown). However, adding additional components, such as Hall effect sensors, requires additional space, which is limited in any implanted device application. Further, using a position detection device adds sources of system failures.

The motor controller 84 switches a series of power switching devices 86 to regulate the stator winding 52 current. In one embodiment, the power switching devices 86 comprise metal oxide semiconductor field effect transistors (MOSFETs).

The embodiment illustrated in FIG. 3 further includes a pump motor speed control circuit 88 coupled to the microcontroller 80 to receive inputs regarding pump operation parameters. The speed control circuit 88 is coupled to the motor controller 84 through a switching device 90, which couples either the speed control circuit 88 or a hardware-implemented "safe mode" speed setting 92, which is independent of the microcontroller 80.

The switching device 90 is actuated by a microprocessor failure detector 94, which may comprise an external "watchdog" timer (not shown) such as a monostable multivibrator, which continuously monitors the microcontroller 80. Any watchdog timers internal to the microcontroller 80 are disabled. Alternatively, the switching device 90 may be actuated by a safety plug 96 which is adapted to plug into either of the controller module connectors 24, 26. The external watchdog timer is periodically reset by the microcontroller 80 during normal controller module 16 operation. In the event that the microcontroller 80 fails, the watchdog timer will not be reset. Upon the watchdog timer expiration, the watchdog timer activates the switching device 90, bypassing the microcontroller 80 and setting the pump 12 to a predetermined speed setting 92. This insures that the pump 12 continues to operate. In a further embodiment, the watchdog timer, upon sensing a failure, triggers an emergency clamp and shuts down the pump 12. The emergency clamp prevents backward flow through the pump 12.

Figure 6:
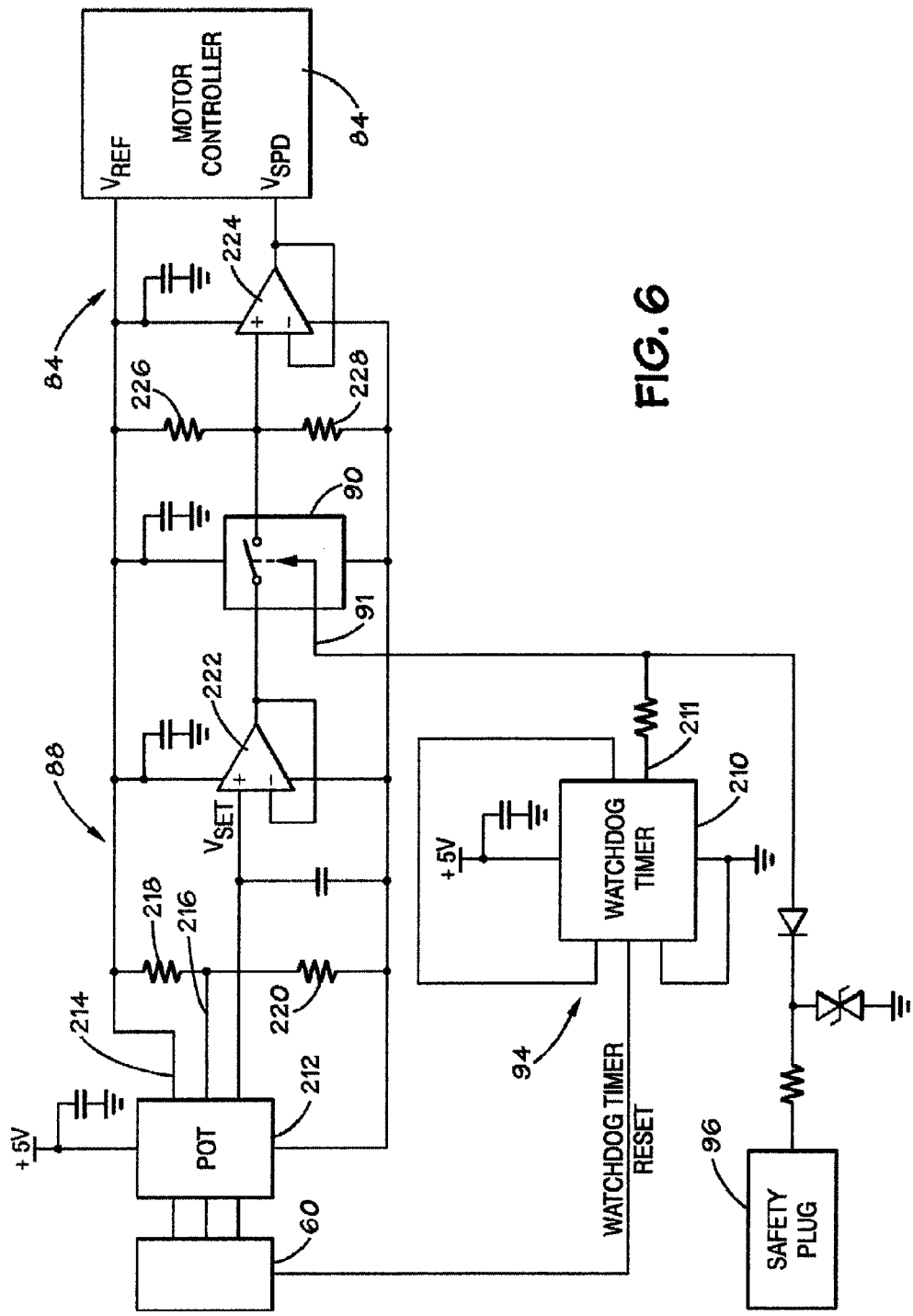
FIG. 6 illustrates an embodiment of an exemplary motor control circuit in accordance with certain teachings of the present disclosure.

FIG. 6 illustrates a schematic diagram of a motor control circuit 200 in accordance with an exemplary embodiment of the invention. The motor speed control circuit 200 includes the motor controller 84, the speed control circuit 88, the fail detector 94, the switching device 90 and the hard code speed 92 from FIG. 3.

The failure detector 94 includes a watchdog timer 210 coupled to the switching device 90. Suitable watchdog timers and switching devices include, for example, a model MAX705 monostable multivibrator and a model MAX4514 single pole-single throw CMOS analog switch, respectively, both available from Maxim Integrated Products. In operation, the output of the watchdog timer 210 is logically high during normal system operation (the microcontroller 80 functioning properly), and logically low when a malfunction or failure of the microcontroller 80 is detected.

During normal operation, the microcontroller 80 periodically provides a watchdog timer reset signal to the input of the watchdog timer 210, which resets the watchdog timer 210, and forces its output 211 logically high. The output 211 of the watchdog timer is coupled to the control input 91 of the switching device 90. In the exemplary embodiment illustrated in FIG. 6, the switching device 90 is configured as a normally open switch. Therefore, the logically high signal at the control input 91 maintains the switching device 90 in a closed state, allowing the microcontroller 80 to control the pump 12 in accordance with user input. If the watchdog timer 210 does not receive its periodic watchdog timer reset signal, after a predetermined time period (for example, one second), it will time-out and its output 211 will toggle from a logically high state to a logically low state. The logically low state at the control input 91 of the switching device 90 will decouple the microcontroller 80 from the motor controller 84 by opening the switching device 90. Alternatively, the switching device 90 may be operated by the safety plug 96 to manually decouple the microcontroller 80 from the motor controller 84.

In the embodiment illustrated in FIG. 6, the motor controller 84 comprises a Micro Linear model ML4425 motor controller. The motor controller 84 includes a voltage controlled oscillator, a pulse width modulated speed control circuit, a commutation logic control circuit, a pulse width modulated current control circuit, MOSFET drivers, a back EMF sampler circuit, and a power fail detector. Additional details regarding the features and operation of the Micro Linear ML4425 motor controller are available in the appropriate Micro Linear specification sheet.

The motor controller 84 further includes an onboard voltage reference $V_{ref}$ and a speed control voltage input $V_{spd}$ that is used as the control reference voltage input for the motor speed control phase-locked loop (PLL). In a typical implementation of a motor controller such as the Micro Linear ML4425 motor controller, predetermined voltage levels of $V_{spd}$ correspond to desired motor speeds, and the voltage level corresponding to the desired motor speed is input to the speed control voltage input $V_{spd}$. With typical motor controller chips, however, motor speed control is based, at least in part, on the relationship between the onboard voltage reference $V_{ref}$ and the speed control voltage input $V_{spd}$. In an embodiment employing the Micro Linear ML4425 motor controller, in accordance with the circuit shown in FIG. 6, the onboard voltage reference $V_{ref}$ output varies from 6.5 volts to 7.5 volts (6.9 volts nominal). Thus, if absolute voltage levels corresponding to desired motor speeds are input to the speed control voltage input $V_{spd}$, the actual pump motor speed may vary as much as ±20%.

To reduce this variation, the speed control circuit 88 shown in FIG. 6 provides a speed control voltage input $V_{spd}$ level that is programmed to some proportion of the onboard voltage reference $V_{ref}$ value, rather than an absolute voltage level. This removes the motor speed control's dependency on the onboard voltage reference $V_{ref}$ output. In a particular embodiment of the invention, this reduces the pump motor speed error from ±20% to approximately ±1%.

In the embodiment illustrated in FIG. 6, the speed control 88 includes a digitally programmable electronic potentiometer 212 that receives inputs from the microcontroller 80. A model X9312T nonvolatile digital potentiometer available from Xicor, Inc. is a suitable digital potentiometer. The "high" terminal 214 of the potentiometer 212 is directly coupled to the onboard voltage reference $V_{ref}$ output of the motor controller 84, and the "low" terminal 216 is coupled to the onboard voltage reference $V_{ref}$ through a voltage divider comprising resistors 218, 220. In a specific embodiment, the resistors 218, 220 comprise 1.02 kΩ and 1.5 kΩ resistors, respectively. The potentiometer 212 thus provides a voltage output $V_{set}$ at its "wiper" terminal that varies from about 0.6×$V_{ref}$ to $V_{ref}$. Allowing the speed control voltage input $V_{spd}$ to equal the potentiometer 212 output voltage $V_{set}$ yields a pump motor speed range of about 7,500 RPM to 12,500 RPM.

The potentiometer 212 output voltage $V_{set}$ is coupled to an input of a first unity gain buffer amplifier 222, the output of which is coupled, during normal operations, through the switching device 90 to an input of a second unity gain buffer amplifier 224. The output of the second unity gain buffer amplifier 224 is connected to the $V_{spd}$ input of the motor controller 84 via a resistive divider comprising resistors 226, 228. The values of resistors 226, 228 should be selected so as to achieve two desired ends: 1.) minimize the loading of the $V_{set}$ signal when the microcontroller 80 is operating normally, and the switching device 80 is therefore closed; and 2.) provide the proper $V_{spd}$ voltage to realize the desired "safe mode" pump motor speed when the switching device 90 is opened via the watchdog timer 210 or the safety plug 96. In one particular embodiment, the predetermined "safe mode" speed setting is 8,500 RPM. Hence, the resistors 226, 228 comprise 31.6 kΩ and 66.5 kΩ resistors, respectively, to achieve a $V_{set}$ value equal to 0.68×$V_{ref}$ when the switching device 90 is open.

The microcontroller 80 may further be programmed with a pump restart feature for restarting the pump 12 in the event of a pump failure. The pump restart leaves the motor speed preset to its latest value. When the restart is activated, the microcontroller 80 initiates a start-up sequence of the motor controller 84, and locks a predetermined time period of pump performance data into the controller module's memory. The controller module memory is discussed further below. If the pump 12 successfully restarts in response to the pump restart feature within a given time limit (10 seconds in one embodiment), a diagnostic alarm is enabled and the motor controller 84 returns the pump 12 to the latest preset speed. If the pump 12 fails to restart, an emergency alarm is enabled and the restart sequence repeats. The microcontroller 80 may be programmed to limit the number of restart attempts. In a particular embodiment, the controller module 16 limits the number of restart attempts to three for a given pump stoppage.

The microcontroller 80 includes a multiple channel analog to digital (A/D) converter, which receives indications of motor parameters from the motor controller 84. Thus, the controller module 16 may monitor parameters such as instantaneous motor current, the AC component of the motor current, and motor speed. In an embodiment of the invention, the controller module 16 incorporates low pass digital filtering algorithms to calculate the mean values of parameters such as motor current to an accuracy of ±1% of full scale.

As shown in FIG. 6, a series of memory devices 122 are additionally coupled to the microcontroller 80 to save system parameters in the event of an emergency, such as a pump shutdown. In one embodiment of the invention, the memory devices comprise three 128K banks of SRAM, which store pump parameters such as pump voltage, current, RPM and flow. The first of the three SRAM banks, segment 0, is the "looping bank," which employs a continuous, circular buffer that continuously stores the current performance data. Upon a predetermined event, such as a pump shutdown and restart, the microcontroller 80 is programmed to transfer the data from the circular buffer to one of the other memory banks.

The second SRAM bank, segment 1, contains the pump performance data prior to the first alarm or restart that occurs after initial power-on or a clearing of segment 0 by the CDAS (CDAS communications with the controller module will be further discussed below). The third bank, segment 2, contains pump performance data prior to the most recent restart event. After each restart event (or any alarm if segment 0 is clear) the data in the active looping bank are transferred to segment 0 or segment 1, as appropriate. For example, following initial start-up, if the pump stops, the processor transfers the data from the memory segment 0, the circular buffer, to memory segment 1. Assume that the pump then restarts. The pump performance data in the circular buffer associated with any subsequent predetermined events are transferred from memory segment 0 to segment 2, such that segment 2 always has the data associated with the most recent pump event.

In one embodiment of the invention, memory segments 0 and 1 each store 55 seconds of pump performance data segments, including pump speed (RPM), voltage, flow rate, instantaneous motor current and time. Further, sample rates for these parameters may be as follows: instantaneous motor current, 2000 samples per second; flow rate, 333 samples per second; pump speed, 10 samples per second; and voltage, 10 samples per second. The sampling resolution for these parameters is eight bits in one embodiment of the invention.

Each memory segment includes predetermined boundaries for each sampled parameter. For example, pump motor current requires 110,000 bytes to store 55 seconds at 2000 samples per second which may be stored in a predetermined memory array. Defining parameter boundaries in this fashion allows a technician to request parametric data by reading a range of blocks. The last block in each memory segment contains time stamp information available from the real-time clock and calendar along with a start and stop memory pointer for each parameter.

A single host computer, such as the system controller 116, may be used to link and control both pumps 12 such that each side may be controlled individually or in a master/slave configuration. Additionally, the clinician may enter any linear or non-linear function describing the desired side-to-side relationship when the system is configured for master/slave operation. Blood flow rate and/or pump speed may be used as the independent and dependent variables respectively.

The system controller 116 features two analog voltage inputs and outputs proportional to pump speed and/or flow. The analog voltage inputs correspond to the desired target pump speed and/or flow and the analog voltage outputs corresponds to the actual pump speed and/or flow.

In certain exemplary embodiments, the control system 116 first establishes serial communication with each pump controller 16 and subsequently requests an Operational Parameters Data Block at a rate of once per second. Upon receipt of the data block, it then extracts the actual pump speed and/or flow from this block of data, and then transmits the necessary number of increment or decrement pump speed commands such that the actual speed and/or flow of the pump tracks the target speed and/or flow. A manual bypass switch on the front panel and a loss-of-power bypass mechanism has been included for safety.

The pumps 12 may thus be controlled in a variety of ways. For example, the common host computer 116 may be programmed to output target reference voltages proportional to the desired left side and right side pump speed or to the desired left side and right side blood flow rate.

A "break-out box" may be used, which is designed to synchronize itself to transmitted requests for the pump's operational parameters and to transparently inject the correct number of increment and decrement pump speed commands such that the actual pumps' speeds match the desired speeds, and/or the desired pump flows match the desired flows. The "break-out box" may operate in any of three primary modes of operation:

a) CDAS Mode whereby an attached clinical data acquisition system (CDAS) is routed directly to its respective VAD Controller 16 and used to provide manual control of the pump 12;

b) "CLCS Mode" whereby an attached clinical data acquisition system establishes a serial communication link with its respective VAD Controller 16 and subsequently provides timing information for the "break-out box" to synchronize itself to. In this mode, the "break-out box" AND clinical data acquisition system are able to directly control pump speed;

P c) CLCS Mode whereby no clinical data acquisition systems are attached and the "break-out box" autonomously establishes it own communication link with the VAD Controller 16 and solely controls the pump's speed.

The "break-out box" can be configured to perform various functions. It can provide visual indication of serial communication and pump status via front panel LED indicators, and/or it can provide a serial data port which transmits system operational information (e.g. current operating mode, number of commands issued, target reference, actual speed/flow, etc.). It can also provide a serial data port through which periodic firmware updates may be programmed negating the need to open the system and replace the processors or processor memories. The status indicators are used to indicate which mode the system is in, receipt of valid or alternate data blocks from attached controllers, pump off information, and the transmission of pump speed increment and decrement commands. In still further embodiments, the "break-out box" also contains a medical-grade power supply to power the attached pumps. The "break-out box" may be manually switched such that the attached clinical data acquisition system may directly control the implanted pumps. The "break-out box" further can be programmed to automatically switch the attached clinical data acquisition system to control the implanted pumps in the event that power to the "break-out box" is removed.

The host computer 116 allows the clinician (user) to control each pump 16 independently or in a master/slave mode. Thus, in various implementations, the left side pump functions as the master and the right side pump functions as the slave and the control variable is pump speed, or the left side pump functions as the slave and the right side pump functions as the slave. The control variable can be pump speed or pump flow, for example. An equation which governs the master/slave relationship may be input into the controller 116. Further, a plurality of governing control equations, each of which is utilized at various operating points within the range of operation, may be used. The equations may be linear or non-linear, single or multivariate, etc.

Preferably, each side's pump information is monitored, displayed, and stored onto a non-volatile memory device (e.g. hard disk drive). Such pump information typically includes pump speed, pump flow, pump current, pump power, left atrial pressure, aortic pressure, right atrial pressure, pulmonary artery pressure, and differential pressure across each pump. Standard clinical pumps and related controllers may be controlled via the attachment of a standard clinical data acquisition system, with control provided by a single host computer executing the desired control algorithm(s). Standard clinical data acquisition systems may remain connected for data monitoring and control purposes concurrently with the host computer. The host computer system may be selectively removed from the control loop and control relinquished to a standard clinical data acquisition system for safety. In some implementations, the single host computer executing the desired control algorithm only controls a single side while manual control is maintained on the other side.

Figure 7:
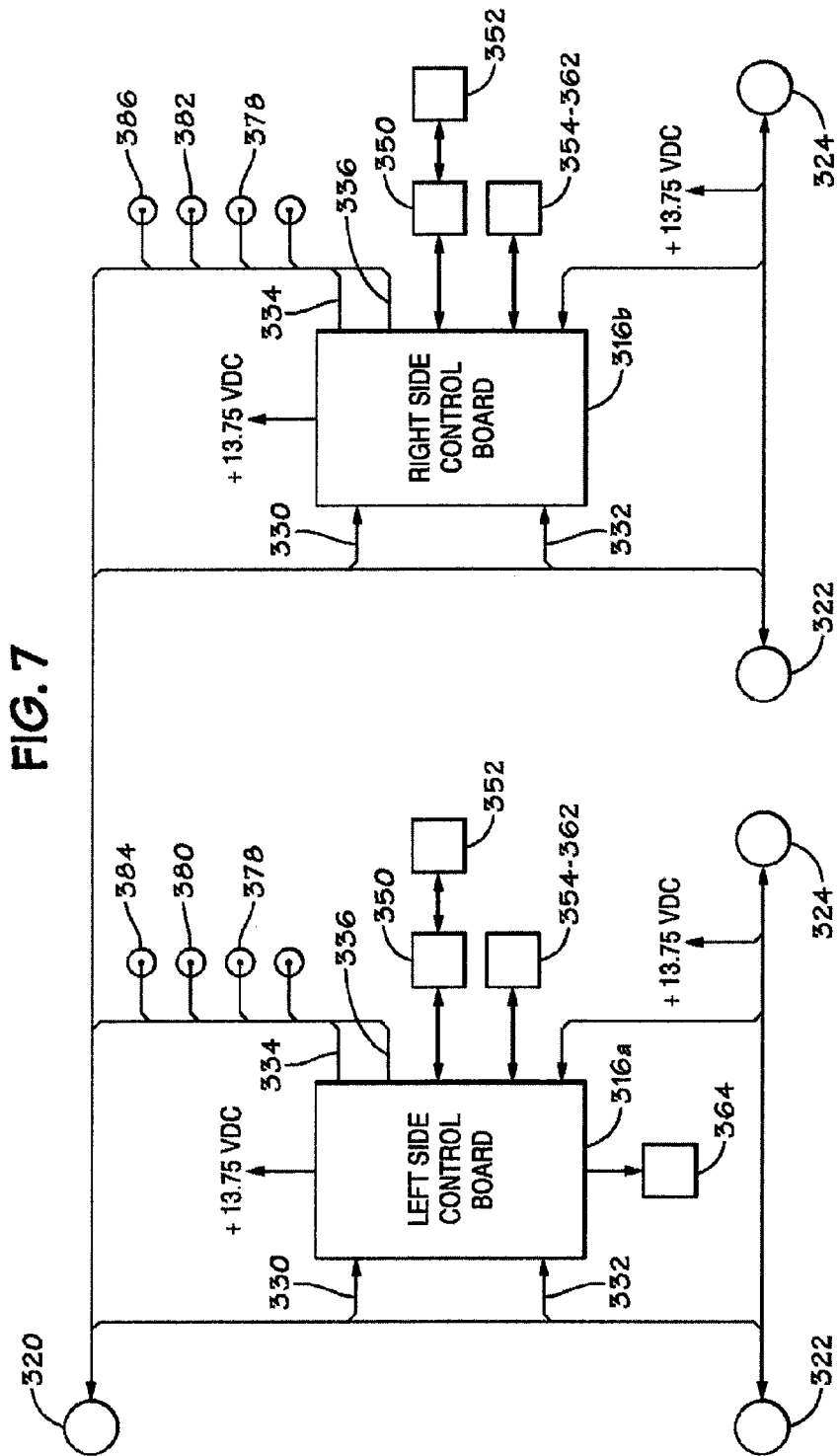
FIG. 7 illustrates an overview of the architecture for an exemplary artificial heart control system in accordance with the teachings of the present disclosure.

FIG. 7 shows a simplified overview of the architecture for an exemplary TAH control system 116. The system 116 includes left and right side closed-loop controllers 316*a*, 316*b*. A 12-pin connector 320 connects the system to an external computer. Additional 12-pin connectors 322, 324 connect the left and right side controllers 316*a*, 316*b* to the left and right side CDASs and left and right side pump controllers. The connectors 322,324 allow the user to attach a CDAS on the left and right side for manual control. Each of the controllers 316*a*, 316*b* includes corresponding speed and serial inputs 330, 332, and speed and power outputs 334, 336.

Figure 8:
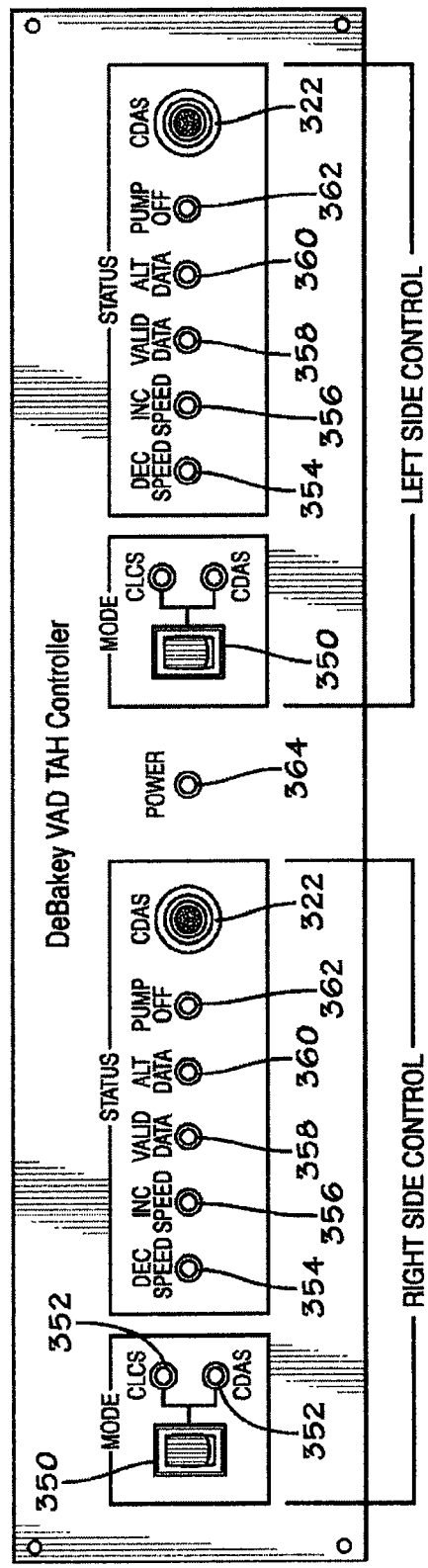
FIG. 8 illustrates details of an exemplary control system front panel.
Figure 9:
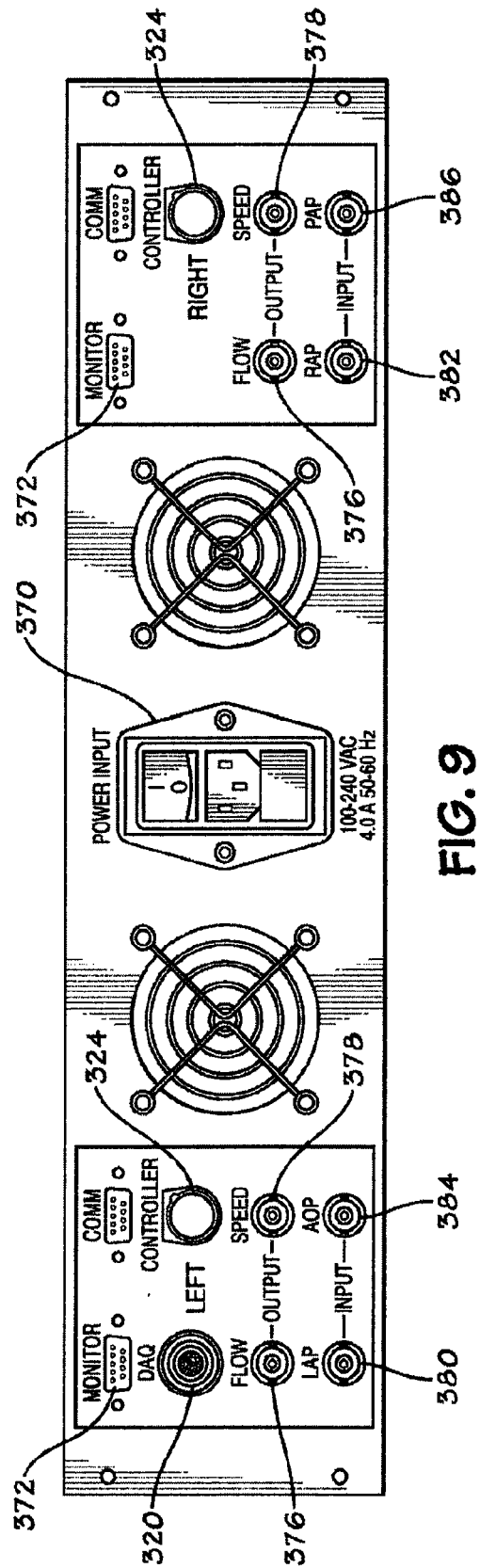
FIG. 9 illustrates details of an exemplary control system rear panel.

FIGS. 8 and 9 detail positions of each controls and indicators on the Control System front panel. The particular control system 116 includes switches that allow the user to manually enter bypass mode, and LED indicators that are used to report which mode the system is in, whether the system is receiving operational parameter blocks or other data, whether the system is transmitting increment or decrement pump speed commands, and if the pumps are off. The following is a detailed list of all of the system's controls and indicators and what their respective functions are:

Front Panel Switches:
  MODE CDAS/CLCS—These two-position rocker switches 350 enable the Control System to actively transmit increment speed and decrement speed commands to each of the VAD Controllers when in "CLCS MODE" or to force the system into its safe bypass mode of operation when in "CDAS MODE".
Front Panel Connectors:
  CDAS—These connectors 322 enable the user to connect a Clinical Data Acquisition System (CDAS) to the system. Communication between the attached CDAS and its respective VAD Controller is achieved when the MODE CDAS/CLCS rocker switch is placed into the CDAS position or when the entire Control System is de-energized.
Front Panel LED Indicators:
  CLCS MODE LED—These LEDs 352 indicate the position of the MODE CDAS/CLCS switch. When in the "CLCS MODE" position, the system will actively transmit increment speed and decrement speed commands to the VAD Controller while in this mode. When the MODE CDAS/CLCS switch is placed into the "CDAS MODE" position, the system is inhibited from transmitting increment speed and decrement speed commands to the VAD Controller while in this mode.
  DEC SPD LED—These amber LEDs 354 flash each time the system transmits a decrement speed command to the VAD Controller.
  INC SPD LED—These amber LEDs 356 flash each time the system transmits an increment speed command to the VAD Controller.
  VALID DATA LED—These green LEDs 358 flash each time the system receives a valid OPERATIONAL PARAMETERS data block transmitted from the VAD Controller. The actual speed and/or flow data is contained in this data block and is subsequently parsed and compared to the sampled analog target reference such that the system can prepare to transmit any necessary increment and/or decrement commands.
  ALT DATA LED—These amber LEDs 360 flash each time the system receives data other than a valid OPERATIONAL PARAMETERS data block transmitted from the VAD Controller. No increment speed or decrement speed commands are transmitted until a valid OPERATIONAL PARAMETERS data block is received.
  PUMP OFF LED—These red LEDs 362 flash each time the system receives a valid OPERATIONAL PARAMETERS data block containing "pump off" information transmitted from the VAD Controller. No increment speed or decrement speed commands are transmitted until a valid OPERATIONAL PARAMETERS data block is received and the pump is running. This prevents the VAD Controller's speed value from being reprogrammed while the pump is off.
  POWER ON LED—This solid green LED 364 is illuminated when the POWER ON/OFF switch is placed into the "ON" position.

FIG. 9 details the position of each connector on the Control System rear panel:
  POWER INPUT—A switched and filtered IEC-320 power entry module 370 is used to connect the Control System to the ac mains using a line cord for the intended country of use.
  MONITOR—DB-9 subminiature connectors 372 are used to download new firmware updates to each side of the Control System 116 and to allow the user to observe system operation using a standard RS-232 serial port monitor configured for 9600 baud operation.
  DAQ—This connector 320 is used to interface the Control System controller module to an external computer, such a a Panel PC mounted on its top enclosure lid. All analog inputs and outputs for monitoring and control of the VADs are routed through this port.
  CONTROLLER—These connectors 324 are used to interface each side's respective VAD Controller 16 with the Control System 116 via in interface cable, such as MicroMed Technology's standard VAD Controller Interface Cable. Power, serial communication, and analog flow and current signals are routed through these ports.
  FLOW—These two connectors 376 are used to route analog flow information from each VAD Controller to an externally attached data acquisition system.

SPEED—These two connectors 378 are used to route analog speed information derived from each VAD Controller's transmitted Operational Parameters Data Block to an externally attached data acquisition system.

LAP—This connector 380 is used to route analog left atrial pressure information from an external pressure transducer to the system's integral Panel PC with analog I/O board installed.

RAP—This connector 382 is used to route analog right atrial pressure information from an external pressure transducer the system's integral Panel PC with analog I/O board installed.

AoP—This connector 384 is used to route analog aortic pressure information from an external pressure transducer the system's integral Panel PC with analog I/O board installed.

PAP—This connector 386 is used to route analog pulmonary artery pressure information from an external pressure transducer to the system's integral Panel PC with analog I/O board installed.

The above description of exemplary embodiments of the invention are made by way of example and not for purposes of limitation. Many variations may be made to the embodiments and methods disclosed herein without departing from the scope and spirit of the present invention.

What is claimed is:

1. A heart pump system, comprising:
   first and second motor driven blood pumps;
   a first motor controller and a second, different motor controller, each controller including a processor and being operably connected to the first and second pumps, respectively; and
   a system controller operably connected to the first and second motor controllers.

2. The system of claim 1, wherein the pumps comprise ventricle assist devices (VADs).

3. The system of claim 1, wherein the system controller operates the pumps in a master slave configuration.

4. The system of claim 1, wherein the first pump is inserted between a patient's left atrium and ascending aorta and the second pump is inserted between the patient's right atrium and pulmonary artery.

5. The system of claim 1, wherein at least one of the pumps replaces at least one of the ventricles.

6. The system of claim 1, wherein the system controller periodically resets a watchdog timer during normal operation.

7. The system of claim 6, wherein the watchdog timer sets the pumps to predetermined speeds upon expiration thereby ensuring that the pumps continue to operate in the event of a system controller failure.

8. The system of claim 6, wherein the watchdog timer triggers an emergency clamp upon expiration thereby preventing backward flow through the pump.

9. The system of claim 1, further including a manual safety which sets the pumps to predetermined speeds thereby ensuring that the pumps continue to operate in the event of a system controller failure.

10. The system of claim 1, wherein the system controller includes memory for storing pump performance data including at least four variables selected from the group consisting of pump speed, voltage, current, flow rate, left atrial pressure, aortic pressure, right atrial pressure, pulmonary pressure, and differential pressure.

11. The system of claim 10, wherein the pump performance data is temporarily stored in a looping buffer where it is overwritten periodically.

12. The system of claim 10, further including a host computer operable to receive the pump performance data and allow a clinician to configure the controller to control each pump independently.

13. The system of claim 1, wherein the system controller operates the pumps independently.

14. A heart pump system, comprising:
    first and second motor driven blood pumps;
    first and second motor controllers, each controller including a processor and being operably connected to the first and second pumps, respectively; and
    a system controller operably connected to the motor controllers, wherein the system controller is operable to independently command the motor controllers using a speed control circuit during normal operation and command the motor controllers using predetermined speed settings during abnormal operation.

15. The system of claim 14, wherein at least one of the pumps replaces at least one of the ventricles.

16. The system of claim 14, wherein the system controller periodically resets a watchdog timer during normal operation.

17. The system of claim 16, wherein the watchdog timer sets the pumps to predetermined speeds upon expiration thereby ensuring that the pumps continue to operate in the event of a system controller failure.

18. The system of claim 16, wherein the watchdog timer triggers an emergency clamp upon expiration thereby preventing backward flow through the pump.

19. The system of claim 16, wherein the rotor of the motor driven blood pumps induces blood flow through the motor driven blood pumps.

20. The system of claim 14, further including a manual safety which sets the pumps to predetermined speeds thereby ensuring that the pumps continue to operate in the event of a system controller failure.

21. A heart pump system, comprising:
    first and second motor driven blood pumps, each pump comprising an electric motor driving a rotor to induce blood flow;
    first and second motor controllers electrically connected to the first and second electric motors, respectively, the first and second motor controllers at least partially embodied in first and second microchips; and
    a system controller operably connected to the first and second motor controllers, the system controller at least partially embodied in a third microchip, wherein the system controller is operable to independently command the motor controllers.

* * * * *